United States Patent [19]

Courtney et al.

[11] 4,311,148
[45] Jan. 19, 1982

[54] MICRO-JEJUNOSTOMY FEEDING TUBE

[75] Inventors: Barry G. Courtney, Chicago; Mitchell V. Kaminski, Jr., Niles, both of Ill.

[73] Assignee: Mitchell V. Kaminski, Jr., Chicago, Ill.

[21] Appl. No.: 151,143

[22] Filed: May 19, 1980

[51] Int. Cl.³ ............................................. A61M 25/00
[52] U.S. Cl. .................................... 128/348; 128/347
[58] Field of Search ............... 128/347, 348, 350, 322, 128/DIG. 26

[56] References Cited

U.S. PATENT DOCUMENTS

| | | | |
|---|---|---|---|
| 3,380,448 | 4/1968 | Sadove et al. | 128/348 X |
| 3,508,545 | 4/1970 | Reif et al. | 128/347 X |
| 3,804,097 | 4/1974 | Rudie | 128/347 X |
| 4,014,317 | 3/1977 | Bruno | 128/348 X |
| 4,033,331 | 7/1977 | Guss et al. | 128/348 X |
| 4,192,305 | 3/1980 | Seberg | 128/348 X |
| 4,196,731 | 4/1980 | Laurin et al. | 128/348 X |

*Primary Examiner*—Gene Mancene
*Assistant Examiner*—Wenceslao J. Contreras

[57] ABSTRACT

An elongated, flexible catheter feeding tube for use in providing nutrition and/or medication directly into the intestine, having a fabric cuff for subcutaneous implantation, a proximal wing for positioning inside the abdominal wall and a distal wing for positioning inside the intestine.

9 Claims, 6 Drawing Figures

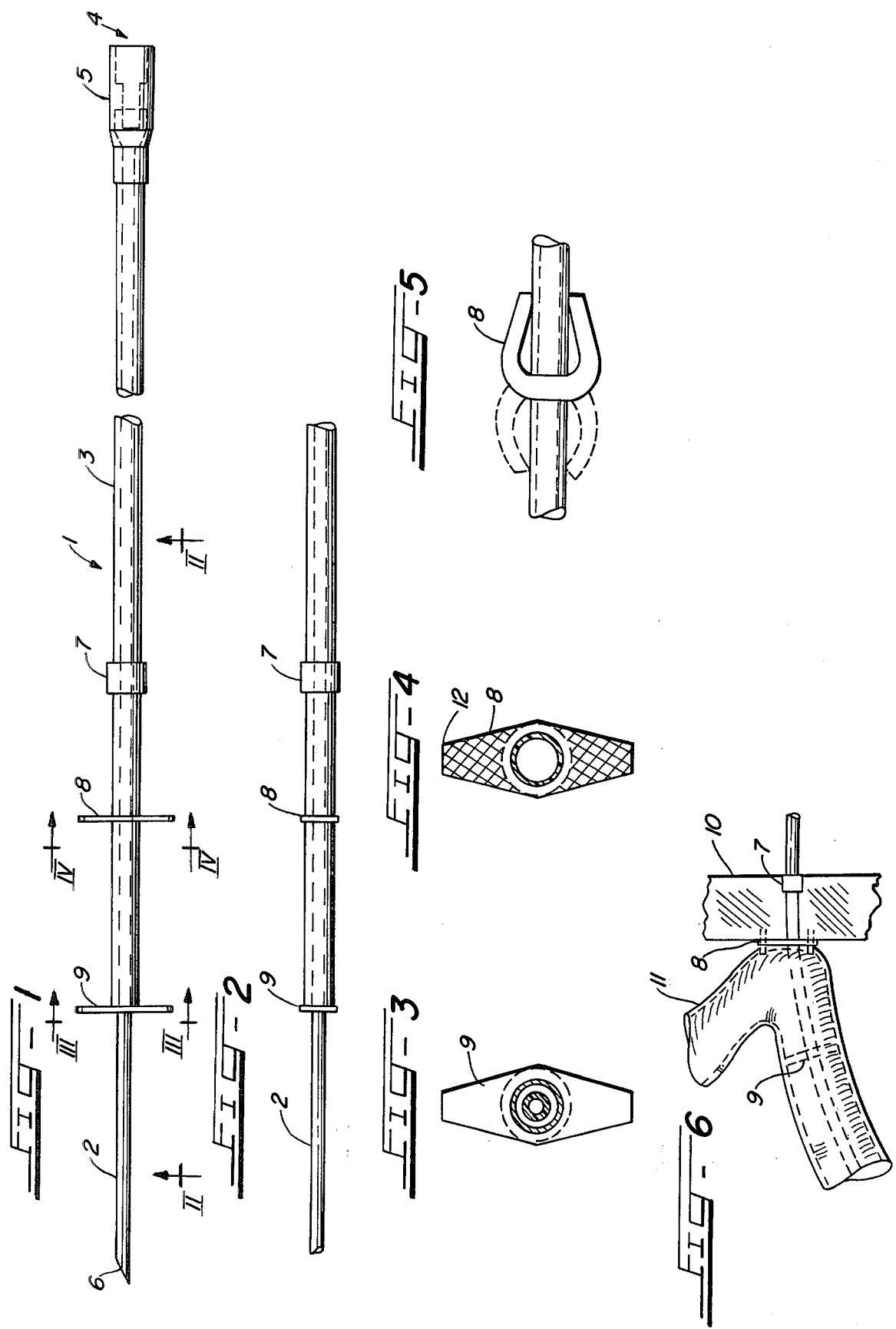

MICRO-JEJUNOSTOMY FEEDING TUBE

BACKGROUND OF THE INVENTION

This invention relates to a tube for direct intestinal feeding. Broadly speaking, the present invention provides a device suitable for providing either nutrition or medication directly to the intestine. The present invention is particularly suitable in cases where nutrition or medication must be supplied frequently over some extended period of time, such as in the case of any patient who has become anorexic due to disease or treatment or one who cannot eat or swallow effectively due to a mechanical or physical handicap.

Known methods of providing nutrition or medication include gastrostomy feeding wherein a feeding tube is implanted directly through the abdominal and stomach wall. The tube, in turn, is sutured to the stomach wall and the stomach wall is, in turn, sutured to the abdominal wall to hold the device in place and prevent the tube from slipping out of the stomach area.

A major problem with gastrostomy feeding is that leakage of digestive juices such as acids and enzymes often occurs around the tube from the stomach to the surrounding skin area; thus, digesting tissue in that area and causing damage, pain, and soilage of clothing.

It is therefore desirable to provide nutrition or medication directly to the small intestine and thus bypass the stomach.

Initial attempts to provide such direct nutrition or medication were to utilize a straight tube, such as a Foley catheter made for urinary bladder drainage and implant it directly into the intestine. The intestine was sutured around the tube to hold the tube in place. Since sutures could not be placed directly through the feeding tube itself, the balloon tip within the intestine is inflated to prevent it from falling out. Further, the intestinal wall is sutured around the tube and the resultant friction between the tube and the intestine is all that holds the tube in place to prevent it from being pulled in by intestinal function. These jerry-rigged tubes are relatively stiff, uncomfortable, and difficult to conceal under clothing. Like gastrostomy tubes, they also leak and cause skin irritation, pain and soilage.

Additionally, if the balloon tip is too large, it can produce blockage causing pain and vomiting. The balloon is quickly digested, causing these tubes to fall out during which time the hole can close, requiring another operative procedure to replace it.

SUMMARY OF THE INVENTION

Accordingly, it is the object of the present invention to provide a direct intestinal feeding tube which can be used to provide nutrition or medication directly to the intestine and thus eliminate problems inherent in jerry-rigging tubes intended for use other than jejunostomy or gastrostomy feeding methods.

Another object is to provide a feeding tube which can remain inserted in the patient for an extended period of time for providing nutrition or medication as needed directly to the small intestine which is comfortable, easily hidden beneath clothing, does not leak and soil, and does not cause an obstruction within the bowel or move in and out.

A further object is to provide a feeding tube which cannot be easily removed either accidentally or intentionally by a patient.

Other objects and advantages of the present invention will become apparent from the following detailed description and upon reference to the drawings in which:

FIG. 1 is a top view of a preferred embodiment of a feeding tube of the present invention;

FIG. 2 is a side elevational view taken along the lines II—II of FIG. 1;

FIG. 3 is a cross-section taken along the lines of III—III of FIG. 1;

FIG. 4 is a cross-section taken along the lines of IV—IV of FIG. 1;

FIG. 5 is an enlarged top view of the wing shown in FIG. 4 in position for insertion or withdrawal;

FIG. 6 is a schematic showing the arrangement of the embodiment depicted in FIG. 1 as it would appear when actually in use.

One embodiment of the feeding tube of the present invention is shown in FIG. 1 and is designated generally by the numeral 1. Feeding tube 1 consists of an inner tube 2 and an outer tube 3 coaxially mounted. Inner tube 2 extends from the feed end 4 where tube 2 is connected to an adapter 5 (for example, a Luer adapter) for attachment to a nutrient or medication source (not shown). The nutrition or medication passes through inner tube 2 through to the discharge end 6. Both the inner and outer tube are made of soft, flexible material such as silicon rubber.

This feeding tube is provided with a fabric cuff 7, a proximal wing 8 and a distal wing 9. The wings are mounted perpendicularly to the tube 1. The cuff 7 is of a construction known in the art and can be made of any material which permits tissue ingrowth immediately subcutaneous to the catheter exit site and further secures the tube and seals the tube to the patient. Suitable materials for the cuff include DACRON ® velour or DACRON ® felt material.

The feeding tube 1 as well as the proximal and distal wings 8 and 9 are preferably made of material that remains innocuous to the tissues of the intestine, the viscera and the abdominal wall. A suitable material is silicon rubber.

The construction of the distal and proximal wings will be described with reference to FIGS. 3 and 4. Wing 8 is made of a resilient material such as silicon rubber so that in its static condition, the normally mounted wing presents the planar configuration as shown in FIG. 4. When either wing 8 or 9 is inserted through the abdominal wall or through the intestine, the wing is folded back along the feeding tube as shown in solid lines in FIG. 5 for wing 8 so as to permit insertion through the smallest possible incision. Wing 8 is passed through an incision in the abdominal wall in the configuration shown in FIG. 5. The resilient wing is then released permitting it to return to the planar configuration shown in FIG. 4. The reverse occurs when the tube is removed as shown in phantom lines in FIG. 5.

It has been found preferable to provide wings tapered toward the extremities as shown in FIG. 3 so as to present less of a planar surface away from tube 1 than immediately adjacent the tube. With such a configuration, the wings are more flexible near the tips than near the tube permitting easier removal.

The method of use of the present invention will now be described with primary reference to FIG. 6, a schematic representation showing a feeding tube of the present invention as implanted through an abdominal wall and into a small intestine. In implanting the tube of the present invention, an incision is made in the abdominal wall 10 and the small intestine 11. Tube 1 is inserted through a separate incision on the abdominal wall lateral to the first incision, tunneled beneath the skin and into the abdominal cavity, until the proximal wing 8 is just inside the abdominal wall and the cuff just beneath the skin. A small incision is made in intestine 11, and the discharge end 6 of the feeding tube is inserted into the intestine. The tube is inserted until the distal wing 9 is just inside the intestine. In inserting the distal wing, the wing 9 is folded back along tube 1 in the same manner as shown in FIG. 5 for proximal wing 8. Once the distal wing 9 is inside the intestine, the wing again unfolds to an open position and the incision in the intestine is closed by suture around feeding tube 1. Since distal wing 9 is provided to prevent movement of the feeding tube out of the intestine 11, the intestine is sutured completely around the peripheral of the feeding tube (a Whitsle tunnel) as in between the proximal and distal wings 9.

The proximal wing 8 is then sutured to the intestine and inner abdominal wall. If the tube is to be permanent, a non-absorbable suture material is used such as nylon or silk. If the need for tube feeding is limited, an absorbable suture material such as catgut or DEXON ® can be used.

Fabric cuff 7 is positioned immediately subcutaneous to the abdominal wall 10. The incision in the abdominal wall is sutured around the area of cuff 7 which allows tissue ingrowth into the cuff; thus, the patient will "grow into" the cuff.

With the feeding tube in place, nutrients or medication can be provided by an appropriate connection at the adapter 5. The feeding tube can remain in place for subsequent usage. When not in use, the tube can be irrigated, capped, and concealed comfortably beneath the clothing.

When medical treatment is no longer necessary, the tube is removed under local anesthesia by first removing tissue from cuff 7 and then simply pulling the tube out while aspirating with a syringe to prevent leakage of tube contents along its course during withdrawal. Both wings 8 and 9 will bend back along the feeding tube when sufficient force is exerted to permit wing 8 to pass through the incision in the abdominal wall and wing 9 to pass through the incision in the small intestine as well as the abdominal wall. Sufficient time should have passed to allow the suture material selected to secure the tube through wing 8 to be absorbed.

In order to minimize the possibility of tube breakage during removal, it has been found preferable to provide a double tube arrangement between distal wing 9 and the adapter 5 as shown in FIG. 1. The embodiment as shown in FIG. 1 is constructed by providing holes in wings 8 and 9 having a circumference equal to the circumference of tube 2. Wing 8 is secured to tube 2 as well as to the section of tube 3 between wing 8 and the feed end and to the section of tube 3 between wing 8 and wing 9 by suitable adhesive such as silicon adhesive medical-type Grade A. In using the adhesive in securing wing 8, the adhesive also secures inner tube 2 and outer tube 3 in fixed relationship and provides a seal between tube 2 and tube 3 which has the added effect of preventing infection emanating at the feed source from proceeding in past the abdominal wall. This also prevents any leakage of abdominal fluid through the area between tubes 2 and 3.

Similarly, wing 9 is secured to the portion of tube 3 between wings 8 and 9 as well as to tube 2 by an adhesive which also forms a seal preventing the spread of infection or the leakage of intestinal fluid.

While the preferred embodiment shown in the attached drawings permits assembly of the present invention with standard tubing, the same result can be achieved by using a single catheter in place of the inner and outer tubes 2 and 3. Such a single catheter is thicker in the area between the feed end 4 and wing 9 to provide the added strength necessary to minimize tube breakage on removal or forced irrigation and of a single wall thickness in the area between wing 9 and discharge end 6, which can also be of a smaller diameter.

The proximal wing 8 is preferably provided with a DACRON ® mesh material 12 integrally formed in the wing as shown in FIG. 4 to permit suturing the wing directly to the abdominal wall and intestine as described above in cases where such added stability is required. If wing 8 is sutured with a non-absorbable material rather than an absorbable material, the removal procedure requires removal of such sutures before removing the feeding tube.

Finally, the feeding tube of the present invention can be made of a radio-opaque material so that the tube will be visible on X-rays; thus permitting the orientation of the tube to be determined.

While the present invention has been described in connection with a preferred embodiment, it will be understood that we do not intend to be limited to the particular embodiment shown but intend on the contrary to cover the various alternative and equivalent forms of the invention included within the spirit and scope of the appended claims.

We claim:

1. An elongated flexible feeding tube having a feed end and a discharge end for use in supplying nutrition or medication directly to the intestine comprising an elongated flexible catheter, a fabric cuff for subcutaneous implantation located on said catheter a distance from the feed end, a proximal wing of resilient material located on said catheter a distance from said fabric cuff toward the discharge end of said catheter equal to or greater than the thickness of the abdominal wall, a distal wing of resilient material located on said catheter a distance from said proximal wing toward said discharge end, both of said wings being mounted perpendicular to said catheter.

2. The feeding tube as claimed in claim 1 wherein said catheter consists of an inner tube extending from the feed end to the discharge end and an outer tube extending from the feed end to the distal wing, said tubes held in fixed relation to each other.

3. The feeding tube as claimed in claim 2 wherein both wings are tapered toward the ends of the wings.

4. The feeding tube as claimed in claim 2 wherein the proximal wing contains a mesh material integrally formed in the wing.

5. The feeding tube as claimed in claim 2 wherein the catheter is made of a radio-opaque material.

6. The feeding tube as claimed in claim 1 wherein the catheter has a smaller outer diameter in the region between the distal wing and the discharge end.

7. The feeding tube as claimed in claim 6 wherein both wings are tapered toward the ends of the wings.

8. The feeding tube as claimed in claim 6 wherein the proximal wing contains a mesh material integrally formed in the wing.

9. The feeding tube as claimed in claim 6 wherein the catheter is made of a radio-opaque material.

* * * * *